United States Patent
Machac, Jr. et al.

(10) Patent No.: US 6,673,212 B2
(45) Date of Patent: Jan. 6, 2004

(54) POLYMERIZATION-INHIBITED DISTILLATION

(75) Inventors: James R. Machac, Jr., The Woodlands, TX (US); Edward T. Marquis, Austin, TX (US); Susan A. Woodrum, Round Rock, TX (US); Ralph M. DiGuilio, Round Rock, TX (US); Mike W. McKinney, Cedar Park, TX (US)

(73) Assignee: Huntsman Petrochemical Corporation, Austin, TX (US)

( * ) Notice: Subject to any disclaimer, the term of this patent is extended or adjusted under 35 U.S.C. 154(b) by 0 days.

(21) Appl. No.: 10/127,286

(22) Filed: Apr. 22, 2002

(65) Prior Publication Data

US 2002/0179426 A1 Dec. 5, 2002

Related U.S. Application Data

(60) Provisional application No. 60/286,596, filed on Apr. 26, 2001.

(51) Int. Cl.$^7$ .......................... B01D 3/34; C07D 493/80
(52) U.S. Cl. ........................ 203/8; 203/91; 203/100; 549/230
(58) Field of Search ....................... 203/8, 100, 91, 203/2, 6, 7; 549/230

(56) References Cited

U.S. PATENT DOCUMENTS

| | | | |
|---|---|---|---|
| 2,773,070 A | | 12/1956 | Lichtenwalter et al. .. 260/340.2 |
| 3,879,288 A | * | 4/1975 | Siegele ........................ 210/701 |
| 4,162,200 A | * | 7/1979 | Himmele et al. ............. 203/58 |
| 4,342,652 A | * | 8/1982 | Schiller et al. ............. 210/698 |
| 6,156,160 A | | 12/2000 | Marquis et al. ............... 203/29 |
| 6,315,868 B1 | * | 11/2001 | Nisoli et al. .................. 203/57 |

* cited by examiner

*Primary Examiner*—Virginia Manoharan
(74) *Attorney, Agent, or Firm*—Christopher J. Whewell

(57) ABSTRACT

Identified herein are inhibitors which may be added to the boiling pot portion of a distillation apparatus prior to or during the distillation of an alkylene carbonate. The inhibitors retard the occurrence of undesirable reactions of the alkylene carbonate with itself and impurities present in the pot, and hence greatly reduce or minimize the formation of undesirable by-products which otherwise tend to reduce overall yields of alkylene carbonate recovered by the distillation process. Higher distillation temperatures at higher pressures over the prior art are possible without attendant losses of significant amounts of recovered alkylene carbonate, which confers heretofore unseen flexibility in alkylene carbonate distillation.

18 Claims, No Drawings

POLYMERIZATION-INHIBITED DISTILLATION

CROSS-REFERENCES TO RELATED APPLICATIONS

This invention claims priority to U.S. provisional patent application No. 60/286,596 which was filed on Apr. 26, 2001, which is currently still pending.

TECHNICAL FIELD

This invention relates to a process for producing high-purity alkylene carbonates. More particularly, it relates to a distillation process in which alkylene carbonate distillates are produced, and in which a reduced amount of polyether polycarbonate impurities are formed during the distillation procedure.

BACKGROUND

Alkylene carbonates are well known materials in the chemical arts which are useful in a wide variety of end uses that include use as solvents, carriers, reactants, etc. owing to the favorable combination of physical and chemical properties they possess. The alkylene carbonates to be purified according to the present invention include those represented by the formula:

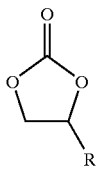

which are the most commonly available alkylene carbonates, having R=hydrogen, methyl, or ethyl; and which correspond to ethylene carbonate, propylene carbonate, and butylene carbonate.

Alkylene carbonates may be produced by differing methods, with the most common commercially practiced method being that which is taught in U.S. Pat. No. 2,773,070 (incorporated herein by reference thereto) in which the catalyst is a tetraalkyl ammonium bromide. Depending upon the exact processing conditions used, the alkylene carbonate product may contain varying degrees of chemical impurities in addition to the desired alkylene carbonate. Thus, distillation is a commonly-employed technique used to purify the alkylene carbonate product.

The distillation of the alkylene carbonate according to the prior art is carried out in accordance with conventional distillation principles, involving a pot, condenser, and receiver. U.S. Pat. No. 6,156,160 (incorporated herein by reference thereto) describes one such method involving several distillation apparati connected to one another in a series arrangement. However, even when using the optimized configuration of equipment and processing conditions of this and other prior art methods, a substantial quantity of the contents of the bottoms in the distillation equipment comprises a polymerized form of the alkylene carbonate being purified, by virtue of its residence time in the distillation pot. The undesirable polymerized form of alkylene carbonate, which is technically considered to be a polyether carbonate exemplified by the structure:

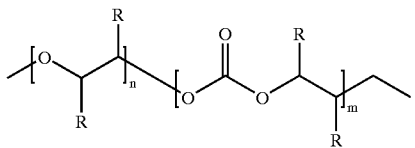

in which the individual R groups may be selected from the group: hydrogen, methyl, or ethyl, and where m and n may each be any integer between 1 and 5000 or greater. This material is believed to be formed by the self-condensation polymerization of the alkylene carbonate during distillation and de-carboxylation of the resulting polymer thus providing a polyethercarbonate impurity which is capable of reacting further yet with another molecule of the alkylene carbonate that is being purified. The result of the continuous auto-polymerization of the alkylene carbonate is that there is an increase in the average molecular weight of the material in the pot, which material includes both the alkylene carbonate being purified and the polymeric autocondensation product. The formation of the polyethercarbonate impurity from the alkylene carbonate being purified results in a reduction of the yield in the amount of desired alkylene carbonate distillate obtainable. Therefore, formation of the polyethercarbonates represents an undesirable side reaction in the distillation of alkylene carbonates because it reduces the total amount of final product obtainable as overheads. Thus, if a method of inhibiting formation of polyethercarbonates in the distillation pot during the distillation process were available, such method would result in increased product yields in the case of alkylene carbonate manufacture.

SUMMARY OF THE INVENTION

The present invention provides a distillation process for purifying alkylene carbonates which comprises the steps of first providing a distillation apparatus which includes a pot portion, a condenser portion, and a receiver portion. An alkylene carbonate is provided in the pot portion of the apparatus, along with an alkylene carbonate autopolymerization inhibiting substance as disclosed herein. An effective amount of heat is supplied to the pot portion to cause said alkylene carbonate to boil to form vapor and the vapor is caused to enter the condenser portion, in which it is condensed to provide purified alkylene carbonate in its liquid form. The liquid state alkylene carbonate is collected in the receiver portion and is recovered from the receiver.

DETAILED DESCRIPTION

According to the present invention, an impure alkylene carbonate material is subjected to purification by distillation, in which the boiling pot which contains the impure alkylene carbonate to be distilled is charged with an effective amount of an inhibitor substance, which inhibitor substance is capable of inhibiting the formation of the polymerized form of the alkylene carbonate.

The practice of the present invention is straightforward, and merely involves the addition of an effective inhibiting amount of an inhibitor substance capable of inhibiting the autopolymerization of the alkylene carbonate undergoing distillation. An inhibitor according to the invention may be added in its neat form, or pre-dissolved in an aliquot of the particular alkylene carbonate to be distilled, or other solvent which will not interfere with the overall purification of the alkylene carbonate.

The concentration of an inhibiting substance provided by the present invention within the contents of the boiling pot is preferably any amount between 0.01% and 1.00% (including every hundredth percentage therebetween) by weight with respect to the total contents of the boiling pot, although higher amounts, up to 10.0% by weight may be used.

The inhibiting substance may be added at any time during the distillation procedure, but is preferably added prior to heating the contents of the boiling pot in which the impure alkylene carbonate to be distilled is contained. Further, it is most preferred that the inhibiting substance be soluble in the alkylene carbonate under conditions of temperature and pressure encountered in the pot during the distillation to the extent of at least 0.05 grams per liter, and more preferably at least 1.0 grams per liter.

One benefit made available by use of the present invention is the ability to employ higher temperatures in the boiling pot than previously used in the prior art, due to elimination of product losses caused by the formation of substantial amounts of the undesirable polyether polycarbonate and de-carboxylation, and loss of carbon dioxide with the co-production of oxide or glycols or polyether carbonates. In accordance with what is known in the prior art, alkylene carbonates decompose upon their being heated to temperatures in excess of about 170° Centigrade. According to the present invention, when using the inhibitors taught herein, pot temperatures as high as 200° C. may be employed. More typically, it is desired in accordance with the invention to use a pot temperature in the range of between 150°–185° C., the use of which temperatures in the absence of an inhibitor provided by the invention would have normally caused formation of significant amounts of polyether polycarbonate. The enablement of economic distillative recovery of alkylene carbonates using such heretofore elevated temperature measures permits greater refining throughput, since the distillation proceeds with greater rapidity at more elevated temperatures. It also means that a pressure more close to atmospheric pressure may be employed during the distillation, which lessens the burden on vacuum equipment and the close monitoring normally associated with its use. However, the present invention does not intend to teach that the useful temperature range for distilling alkylene carbonates is narrowed in any sense using the inhibitors provided herein, but on the contrary rather extends the useful range of temperatures over which alkylene carbonates may be purified by distillation by elimination of an undesirable by-product when higher temperatures are used.

Neither does the present invention intend to teach that the useful pressure range for distilling alkylene carbonates is narrowed in any sense using the inhibitors provided herein, but on the contrary rather extends the useful range of pressures over which alkylene carbonates may be purified by distillation by elimination of an undesirable by-product when higher temperatures associated with higher pressure distillations are used.

According to one preferred form of the invention, the alkylene carbonate autopolymerization inhibiting substance comprises tartaric acid, which is added to the distillation pot at an initial concentration of 0.1 to 0.5% by weight based upon the total weight of the contents of the distillation pot, and the alkylene carbonate comprises ethylene carbonate, which is distilled at 180° C. and at a pressure of 100–125 mm Hg. In the case of ethylene carbonate, tartaric acid is added the distillation pot at an initial concentration of 0.5% by weight based upon the total weight of the contents of the distillation pot, and the ethylene carbonate is distilled at 180°–195° C. at a pressure of 115–120 mm.

Suitable inhibiting substances according to the invention include carboxylic acids. Among those useful are the acids or anhydrides of: fumaric acid, maleic acid, tartaric acid, malic acid, with tartaric acid being most preferred. However, various other materials which contain an organic acid function are useful as autopolymerization inhibiting substances according to the invention. Table I below sets forth the results of the distillation of ethylene carbonate under conditions of elevated temperature with respect to the temperatures employed in its industrial-scale distillation:

TABLE I results of distillation of ethylene carbonate in the presence of various autopolymerization inhibiting substances.

| Run | Inhibitor Acid | $K_1$ | Mol. Wt. | Wt. % inhibitor | millimoles Inhibitor | $f$ | % overhead | Moles $CO_2$ lost |
|---|---|---|---|---|---|---|---|---|
| 1 | None | — | — | — | — | — | 71.4 | 4.5 |
| 2 | Citric | 7.5e-4 | 192.1 | 0.20 | 1.04 | 3 | 73.6 | 0.82 |
| 3 | Citric | 7.5e-4 | 192.1 | 0.30 | 1.56 | 3 | 81.5 | 2.8 |
| 4 | Citric | 7.5e-4 | 192.1 | 0.50 | 2.60 | 3 | 84.2 | 1.4 |
| S | Citric | 7.5e-4 | 192.1 | 0.70 | 3.65 | 3 | 84.4 | 1.8 |
| 6 | d-tartaric | 9.2e-4 | 150.9 | 0.50 | 3.33 | 2 | 97.2 | 0.41 |
| 7 | l-tartaric | 9.2e-4 | 150.9 | 0.50 | 3.33 | 2 | 96.9 | 0.55 |
| 8 | Maleic | 1.2e-2 | 116.1 | 0.50 | 4.31 | 2 | 98.2 | 0.51 |
| 9 | Oxalic | 5.4e-2 | 90.0 | 0.50 | 5.56 | 2 | 62.6 | 4.4 |
| 10 | Succinic | 6.2e-5 | 118.1 | 0.50 | 4.20 | 2 | 49.0 | 7.3 |
| 11 | Fumaric | 9.6e-4 | 116.1 | 0.50 | 4.30 | 2 | 97.3 | 0.23 |
| 12 | Benzoic | 6.1e-5 | 122.1 | 0.50 | 4.10 | 1 | 49.5 | 5.7 |
| 13 | Salicylic | 1.1e-3 | 138.1 | 0.50 | 3.62 | 1 | 83.5 | 2.8 |
| 14 | Decanoic | | 172.3 | 0.50 | 2.90 | 1 | 51.1 | 6.7 |
| 15 | Palmitic | | 256.4 | 0.50 | 1.95 | 1 | 69.9 | 3.9 |
| 16 | Lauric | | 200.3 | 0.50 | 2.50 | 1 | 70.9 | 4.4 |
| 17 | Stearic | | 284.5 | 0.31 | 1.10 | 1 | 66.7 | 4.6 |
| 18 | Aspartic | | 133.1 | 0.50 | 3.76 | 1 | 24.8 | 11.9 |

The data in table 1 were generated by charging 2500 grams of ethylene carbonate into a 5 L flask which was set up for distillation, and then applying heat and distilling the ethylene carbonate in the presence of the autopolymerization inhibiting substance listed. The % overhead value represents, on a percentage basis, the amount of distillate ethylene carbonate recovered. In all cases where the % overhead is lower than 100%, the difference can be attributed to the loss of ethylene carbonate through its decomposition into carbon dioxide and other decomposition products. The % overhead is determined by weighing the distillate and comparing its mass to the original charge.

The Moles of $CO_2$ Lost were measured by subtracting the mass of the distillate collected from the amount of alkylene carbonate charged to the pot, and dividing by the molecular weight of carbon dioxide, 44.

The distillations for which data are set forth in Table I were conducted at a pressure in the range of 95–120 mm Hg and a temperature range of 175°–185° C., whereas commercial distillation of ethylene carbonate is conducted at reduced pressures on the order of 5 to 50 mm Hg and over a temperature range of only 110° to 160° C. The low % overhead value of 71.4% for ethylene carbonate distilled in the absence of an inhibitor shows that distillation of ethylene carbonate conducted under the conditions used in generating the Table I data results in what would be a commercially-unacceptable loss in yield for an industrial-scale process for distilling ethylene carbonate at such elevated temperatures, owing to the formations of polycarbonates, polyethercarbonates, and the like. However, as the data in Table I show, it is now feasible in the presence of some of the inhibitors of the invention to achieve % overhead values over 98%, which is an indication of beneficial inhibition of the formation of decomposition products normally found in alkylene carbonates which have been subjected to such high temperatures.

From Table I it is seen that the distillation of ethylene carbonate in the absence of an inhibitor according to the invention results in the loss of 4.5 moles of carbon dioxide for the 2500 gram charge of ethylene carbonate that was distilled under the conditions aforementioned. Since the charge amount of ethylene carbonate is the same for each run listed in Table I, the value of 4.5 moles of $CO_2$ serves as a gauge for determining whether a given inhibiting substance provides a higher or lower yield of ethylene carbonate distillate. This is because the appearance of $CO_2$ results from the decomposition of the ethylene carbonate; thus, the more $CO_2$ formed, the less ethylene carbonate which will be available to distill over, and the more decomposition products present in the distillation pot to react with the ethylene carbonate present to form polymerization and other by-products, further reducing the potential overall yield. Therefore, every inhibitor acid listed which has a Moles $CO_2$ Lost value of less than 4.5 shows an improved result over the prior art cases where no inhibitor at all is used. Materials listed as inhibiting substances for which the Moles $CO_2$ Lost value is greater than 4.5 are not inhibiting substances at all, but rather can be thought of as being promoters of the decomposition of ethylene carbonate under the conditions employed. Such substances include benzoic acid, succinic acid, decanoic acid, stearic acid, and aspartic acid. Lauric acid and oxalic acid show only marginal improvements over the case when no inhibitor is used.

It is noteworthy that there is no direct relationship between the total molar amount of carboxylic acid units present in the inhibiting substance relative to the amount of ethylene carbonate being distilled and the inhibition or promotion of the formation of carbon dioxide, on a molar basis. Thus, merely increasing the number of carboxylate groups present in the distillation pot is seen to not necessarily inhibit or promote the formation of carbon dioxide over the course of the distillation. This is evident from comparing many of the results above. For example, comparing the moles of $CO_2$ lost in run 12 having 4.10 moles of —COOH present with the molar amount of $CO_2$ lost in run 2, for which there are 3.12 moles —COOH present (3×1.04) shows that while run 12 has about 33% more —COOH groups present, the amount of $CO_2$ lost in run 12 is about 7 times that of run 2. A similar comparison is readily made between runs 10 and 11 in which approximately equal amounts of —COOH are present in each, yet the moles of $CO_2$ lost differ markedly for each case.

It is also noteworthy that there is no direct relationship between the acid strength of the acid used (first dissociation constant $K_1$) as an inhibiting substance and the inhibition or promotion of the formation of carbon dioxide. For example, runs 6 and 8 both show about the same amount of $CO_2$ lost; yet there is a tenfold difference in their first acid dissociation constant.

An idea of the unpredictable nature of the inhibitors of the invention can be observed by comparing the dramatic difference in the amount of $CO_2$ lost results in runs 10 and 11, in which the only difference in the structure is the saturation of the double bond in the case of succinic acid. In succinic acid, the number 2 and 3 carbon atoms are free to rotate about the bond which joins them, and many conformational isomers of succinic acid exist, whereas in the case of fumaric acid, the number 2 and 3 carbon atoms are double bonded to one another and hence not free to rotate, and the molecule is generally planar. The present inventors have no explanation for this unexpected beneficial behavior of fumaric acid over succinic acid with regard to inhibition of the decomposition of ethylene carbonate under the conditions of the distillation used to generate the data in table I.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. Accordingly, the presently disclosed invention is intended to cover all such modifications and alterations, and is limited only by the scope of the claims which follow.

What is claimed is:

1. A distillation process for purifying aklylene carbonate comprising the steps of;
    a) distilling an alkylene carbonate in a distillation apparatus which includes a pot portion, a condenser portion, and a receiver portion;
    b) introducing the alkylene carbonate in said pot portion of said apparatus;
    c) introducing an alkylene carbonate autopolymerization inhibiting substance in said pot portion of said apparatus;
    d) supplying an effective amount of heat to said pot portion to cause said alkylene carbonate to boil, conveying alkylene carbonate vapors to said condensor portion thus forming liquid state alkylene carbonate; and
    e) collecting at least a portion of said liquid state alkylene carbonate distillate in said receiver portion.

2. A process according to claim 1 further comprising the step of recovering distilled alkylene carbonate from said receiver.

3. A process according to claim 1 wherein the alkylene carbonate is selected from the group consisting of ethylene carbonate, propylene carbonate, and butylene carbonate.

4. A process according to claim 1 wherein said distillation process takes place at a pressure in a range of 1 torr to 760 torr.

5. A process according to claim 1 wherein said distillation process takes place at a temperature in a range of 50 degrees centigrade and 170 degrees centigrade.

6. A process according to claim 1 in which said distillation process takes place at a temperature in excess of 170 degrees centigrade.

7. A process according to claim 1 in which said distillation process takes place at a temperature in excess of 180 degrees centigrade.

8. A process according to claim 1 in which said distillation process takes place at a temperature in excess of 190 degrees centigrade.

9. A process according to claim 1 wherein said inhibiting substance is present in an effective inhibiting amount to preclude the formation, of amounts in excess of 5% by weight based upon the amount of alkylene carbonate distilled, of non-alkylene carbonate by-products in said pot portion during said distillation.

10. A process according to claim 1 wherein said alkylene carbonate autopolymerization inhibiting substance is an organic compound which comprises a carboxylate functional group.

11. A process according to claim 1 wherein the alkylene carbonate autopolymerization inhibiting substance is soluble in said alkylene carbonate to the extent of at least 0.05 grams per liter at a temperature at which the alkylene carbonate in distilled.

12. A process according to claim 10 wherein the organic compound further comprises at least one hydroxy group as part of its molecular structure.

13. A process according to claim 1 wherein said alkylene carbonate autopolymerization inhibiting substance comprises a monocarboxylic acid having between 2 and 20 carbon atoms per molecule.

14. A process according to claim 1 wherein said alkylene carbonate autopolymerization inhibiting substance comprises a di-carboxylic acid having between 2 and 20 carbon atoms per molecule.

15. A process according to claim 1 wherein said alkylene carbonate autopolymerization inhibiting substance comprises a tri-carboxylic acid having between 2 and 20 carbon atoms per molecule.

16. A process according to claim 1 wherein said alkylene carbonate autopolymerization inhibiting substance comprises a carboxylic acid selected from the group consisting of citric acid, salicylic acid, and palmitic acid.

17. A process according to claim 1 wherein said alkylene carbonate autopolymerization inhibiting substance comprises a carboxylic acid selected from the group consisting of maleic acid, tartaric acid, malic acid, and fumaric acid.

18. A process according to claim 1 wherein said alkylene carbonate autopolymerization inhibiting substance comprises a carboxylic acid anhydride selected from the group consisting of maleic acid anhydride, tartaric acid anhydride, malic acid anhydride, and fumaric acid anhydride.

* * * * *